US00PP25008P3

(12) United States Plant Patent
Pinochet

(10) Patent No.: US PP25,008 P3
(45) Date of Patent: Oct. 28, 2014

(54) **VARIETY OF *PRUNUS* ROOTSTOCK NAMED 'APRIMED'**

(50) Latin Name: *(Prunus besseyi×P. armeniaca)×P. cerasifera*
Varietal Denomination: Aprimed

(75) Inventor: Jorge Pinochet, Barcelona (ES)

(73) Assignee: Agromillora Iberia, S.L., Barcelona (ES)

( * ) Notice: Subject to any disclaimer, the term of this patent is extended or adjusted under 35 U.S.C. 154(b) by 182 days.

(21) Appl. No.: 13/573,376

(22) Filed: Sep. 12, 2012

(65) Prior Publication Data

US 2014/0075618 P1 Mar. 13, 2014

(51) Int. Cl.
*A01H 5/00* (2006.01)

(52) U.S. Cl.
USPC ..... Plt./180

(58) Field of Classification Search
USPC ..... Plt./180
See application file for complete search history.

*Primary Examiner* — Wendy C Haas
(74) *Attorney, Agent, or Firm* — The Webb Law Firm

(57) ABSTRACT

A new and distinct hybrid plum-apricot plant used as a rootstock that exhibits root-knot nematode resistance, high tolerance to root asphyxia, and compatibility with apricot and plum varieties.

4 Drawing Sheets

Botanical classification: (*Prunus besseyi×P. armeniaca*)× *P. cerasifera.*
Varietal denomination: 'Aprimed'.

BACKGROUND OF THE INVENTION

The present invention comprises a new and distinct cultivar of a plum-apricot hybrid (*Prunus besseyi×P. armeniaca*)×*P. cerasifera* used as a rootstock known by the varietal name 'Aprimed'. The new variety was discovered in Barcelona, Spain in 2000 as a result of a planned breeding program. The new variety is the result of a cross between an unknown clone of (*P. besseyi×P. armeniaca*) (female parent, unpatented) with an unknown clone of *P. cerasifera* (male parent, unpatented). The purpose of the breeding program was to develop a medium vigor rootstock that is well adapted to Mediterranean conditions, compatible with apricot varieties, and that has a high tolerance to poorly drained heavy soils that suffer from water logging conditions. The new variety exhibits similar good tolerance to calcareous soils, high resistance to root-knot nematodes, and resistance to several soil-borne fungi, especially *Rosellinia necatrix.* The genotype has medium chilling requirements and good productivity. It differs from both parents in its leaf shape and medium vigor. Further, the clone does not emit suckers (root and crown) and tolerates water logging conditions better than its plum-apricot parents. Additionally, the new variety is similar to 'Marianna 29624' (unpatented) (*Prunus cerasifera×P. munsoniana*) by exhibiting good compatibility with apricot varieties, root-knot nematode resistance, and good productivity. However, 'Aprimed' differs in vigor from 'Marianna 2624', better tolerance to iron chlorosis, and absence of suckering. The new variety has been field tested and has been found to retain its distinctive characteristics and remain true to type through successive propagations. The following characteristics distinguish 'Aprimed' from other varieties known to the breeder:

1. Medium tree size with a capacity to control vigor;
2. High tolerance to root asphyxia;

3. Better tolerance to alkaline soils than most apricot and plum rootstocks;
4. Resistance to *Rosellinia necatrix* (soil-borne fungus);
5. Highly resistant to root-knot nematodes (*Meloidogyne* spp.);
6. Does not emit root, nor crown suckers;
7. Induces a sustained production from year to year; and
8. Medium chilling requirements within the range of 600 to 800 cu.

DESCRIPTION OF THE DRAWINGS

The accompanying photographic drawings illustrate the new variety with the color being as nearly true as is possible with color illustrations of this type.

DESCRIPTION OF THE PLANT

Figure 1:
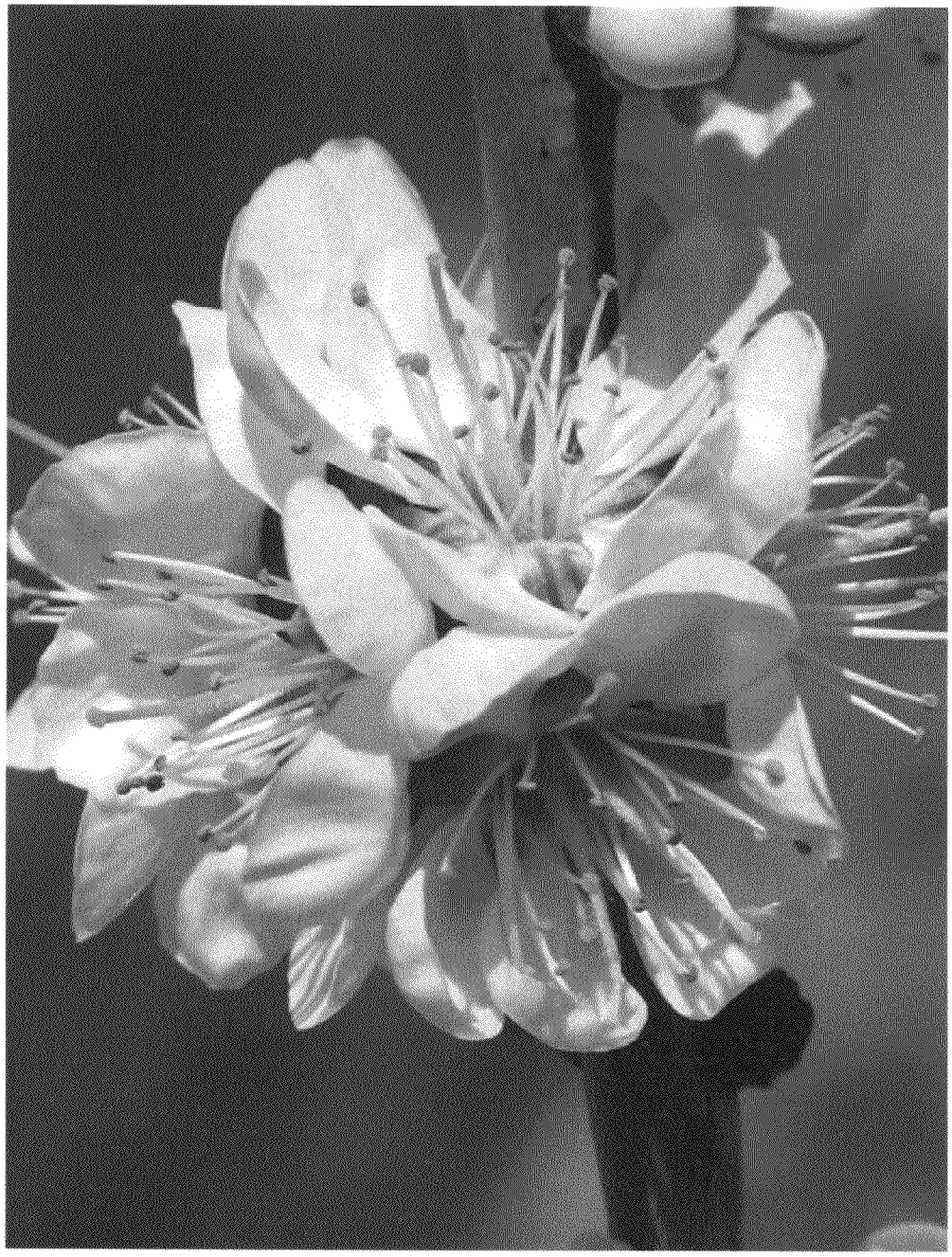
FIG. 1 shows the flowers of the new variety.
Figure 2:
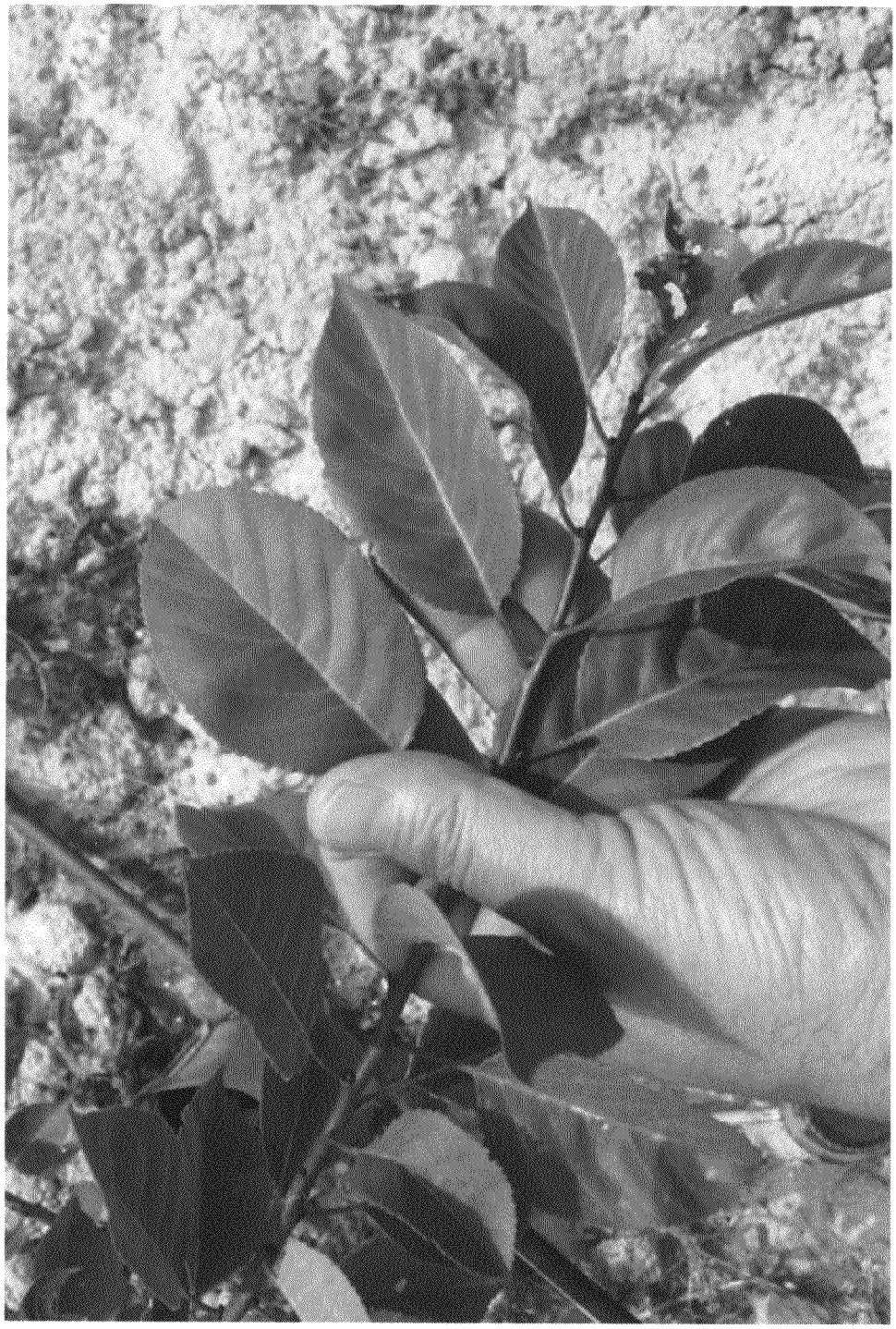
FIG. 2 shows the stem and leaves of the new variety.
Figure 3:
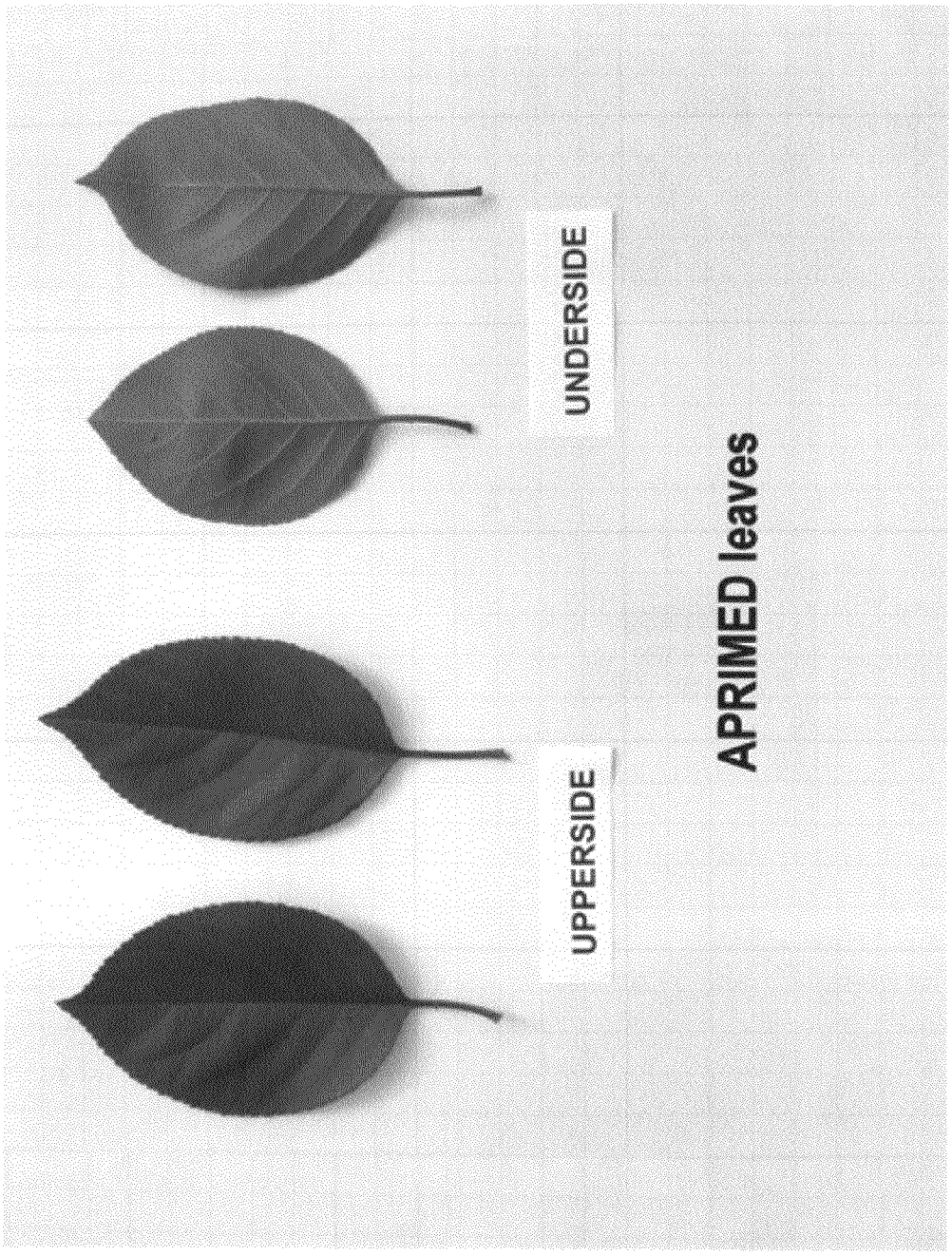
FIG. 3 shows upper and underside of leaves.
Figure 4:
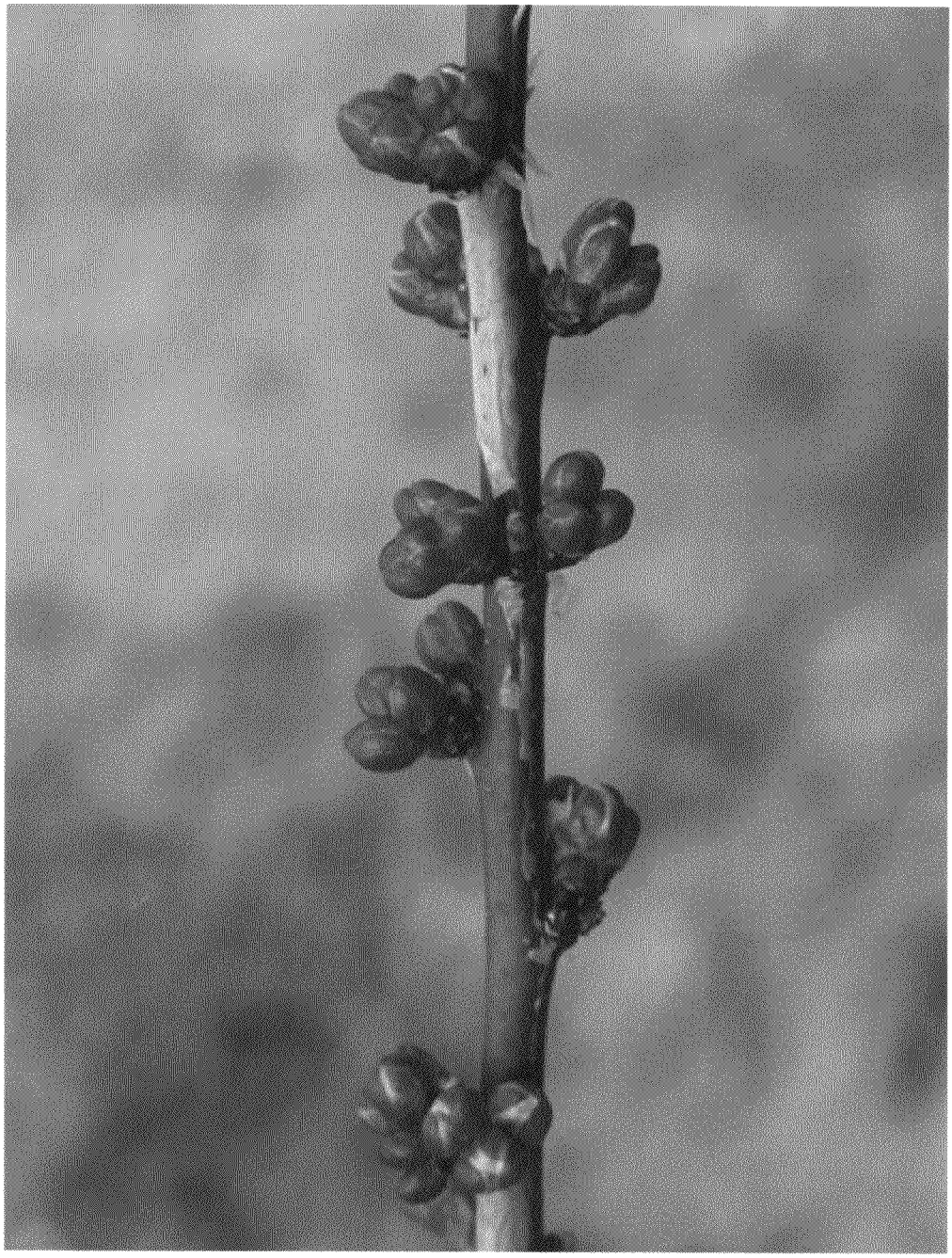
FIG. 4 is a close-up view of stem and flower buds of the new variety.

The following detailed description sets forth the characteristics of the new cultivar. The data which defines these characteristics was collected under natural daylight on plants produced by asexual reproductions via in vitro propagation carried out in Barcelona, Spain in October of 2000. The plants were grown under normal field conditions with drip irrigation and in 40 liter containers. Color designations are presented with reference to the "Dictionary of Color" by A. Maerz and M. Rea Paul, Second Edition (1950).

TREE

Age: 6 years.
Size: 2.1 meters tall.
Vigor: Medium.
Density: Medium.

Form: Compact.
Production: Medium to abundant.
Growth type: Upright and spreading.
Bearing: No fruit bearing.
Pathogen resistance:
*Fungal disease.*—*Phytophthora* spp.
*Insects.*—Unknown.
*Mites.*—Unknown.
*Viruses.*—Unknown.
*Other diseases.*—Root-knot nematodes (*Meloidogyne* spp.).
Rootstock performance:
*Root sprouts* (*suckering*).—Not present.
*Anchorage.*—Good, with a fibrous root system.
*Compatibility.*—Apricot and plum (European and Japanese plum).
*Vigor.*—Medium (20-30% less than 'Marianna 2624').
Trunk:
*Size.*—Perimeter of 30 cm.
*Surface texture.*—Fairly smooth with longitudinal scarf-skin and horizontally oriented lenticels.
*Bark color.*—Plate 8, C 7.
*Lenticels.*—Length: 3 to 6 mm. Width: 1 to 1.5 mm. Color: Plate 15, C 2 (English Grey, Crag). Density: Low.
Branches:
*Diameter.*—Variable; from 0.5 cm to 1.3 cm in the same season.
*Surface texture.*—Smooth in the current season.
*Color.*—Plate 7, E 10 (Chestnut).
*Form.*—Circular in diameter.
*Average angle.*—Acute.
*Bud arrangement.*—Helicoidal throughout the branch.
*Lenticels.*—Length: 1 to 2 mm. in the first year of growth and 2 to 5 mm. in the second year. Width: 0.5 to 1.5 mm. Shape: Younger tissue is initially rounded, turning into elongated horizontally as the branches mature into the season. Density: Medium and increasing as maturity advances. Color: Plate 46, A 2 (Frost Grey, Chateau Grey).
Leaves:
*Length.*—7 to 9 cm. (end of season).
*Width.*—4 to 5.5 cm.
*Form.*—Broadly elliptic.
*Texture.*—Smooth.
*Thickness.*—Medium.
*Base.*—Acute.
*Apex.*—Acute to pointed.
*Margin.*—Between crenate and serrate (mixed and not well defined).
*Pubescence.*—Upper surface: Absent. Lower surface: Absent.
*Color.*—Young leaves: Upper surface: Plate 23, C 12 (Brunswick Green). Lower surface: Plate 23, A 5. Mature leaves: Upper surface: Plate 23, E 7. Lower surface: Plate 22, B 6 (Palmetto).
*Petiole.*—Shape: Straight with central groove along the upper side with 2 small nectaries at the base of the leaf. Length: 19 to 22 mm. Diameter: 1.5 to 2 mm. Color: Plate 7, J 9 (Tanagra, Castilian Brown).
*Veins.*—Venation type: Tree-type disposition. Color: Upper surface: Plate 7, J 9 (Tanagra, Castilian Brown) changing gradually to Plate 14, L 1 (Palm Leaf). Lower surface: Plate 7, H 9 (Live Brown, Autumn Oak) changing gradually to light green tones Plate 21, C 2 (Tea Green).
Flower buds:
*Pedicel.*—Length: 4 to 8 mm. Diameter: 0.8 to 1 mm. Color: Plate 44, B 3 (Irisglow).
*Bud.*—Length: 4 to 5 mm. Width: 2 to 4 mm. Shape: Rounded to ovoid. Color: Plate 6, K 8 (Saraband).
Flowers:
*Bloom timing.*—End of February to the first week of March in Barcelona, Spain.
*Blooming period.*—10 to 12 days.
*Pollination requirements.*—None.
*Number of flowers per raceme.*—Normally two present.
*Fragrance.*—Not perceptible.
*Petals.*—Number: 5. Length: 8 to 10 mm. Width: 7 to 9 mm. Shape: Rounded. Aspect: Cupped upwards and inwards. Margin: Undulate. Texture and appearance: Smooth.
*Color.*—When opening: Upper surface: Plate 1, A 1. Lower surface: Plate 1, B 1. Fully opened: Upper surface: Plate 1, A 1. Lower surface: Plate 1, A 1.
*Sepals.*—Shape: Rounded. Margin: Smooth. Texture: Pubescence present. Length: 3 to 4 mm. Width: 2 to 3 mm. Color: Upper surface: Plate 6, L 8 (Dark Cardinal). Lower surface: Plate 14, L 1 (Palm Leaf).
*Stamens.*—Number (per flower): 24 to 30. Filament length: 8 to 9 mm.
*Anthers.*—Shape: Kidney-shaped. Length: 1 to 1.5 mm. Color: Plate 12, J 5 (Light Stone).
*Pollen.*—Color: Plate 11, J 4 (Mustard). Amount (generally): Abundant.
*Pistils.*—Length: 12 to 14 mm.
*Style.*—Length: 10 to 11 mm. Color: Plate 12, F 1.
*Stigma.*—Shape: Rounded. Color: Plate 12, L 1 (Oil Y.).
Fruit: None produced.
Use: As a medium vigor rootstock that is highly compatible with apricots, but can also be used for plums.
Tree winter hardiness: Hardy (under the conditions in Spain).
Bud winter hardiness: High.
Tolerance to root asphyxia: Highly tolerant.
Tolerance to iron chlorosis: Tolerant.
Drought tolerance: Moderately tolerant.
Disease resistance: Highly resistant to root-knot nematodes.

I claim:

1. A new and distinct variety of hybrid plum-apricot plant, as illustrated and described herein.

* * * * *

UNITED STATES PATENT AND TRADEMARK OFFICE

CERTIFICATE OF CORRECTION

PATENT NO. : PP25,008 P3
APPLICATION NO. : 13/573376
DATED : October 28, 2014
INVENTOR(S) : Jorge Pinochet It is certified that error appears in the above-identified patent and that said Letters Patent is hereby corrected as shown below:

Column 1, Background of the Invention, Line 28, delete "'Marianna 29624'" and insert -- 'Marianna 2624' --

Signed and Sealed this
Tenth Day of March, 2015

Michelle K. Lee

Michelle K. Lee
*Deputy Director of the United States Patent and Trademark Office*